US008073205B2

(12) United States Patent
Shinohara

(10) Patent No.: US 8,073,205 B2
(45) Date of Patent: Dec. 6, 2011

(54) DEVICE AND METHOD FOR CREATING RETINAL FUNDUS MAPS

(75) Inventor: Takao Shinohara, Chofu (JP)

(73) Assignee: KOWA Company, Ltd., Nagoya-Shi, Aichi (JP)

( * ) Notice: Subject to any disclaimer, the term of this patent is extended or adjusted under 35 U.S.C. 154(b) by 751 days.

(21) Appl. No.: 12/210,501

(22) Filed: Sep. 15, 2008

(65) Prior Publication Data

US 2009/0136100 A1 May 28, 2009

(30) Foreign Application Priority Data

Nov. 8, 2007 (JP) ................................ 2007-290685

(51) Int. Cl.
*G06K 9/00* (2006.01)
(52) U.S. Cl. .................... 382/117; 382/128; 382/133
(58) Field of Classification Search .............. 382/117, 382/128, 133
See application file for complete search history.

(56) References Cited

U.S. PATENT DOCUMENTS 5,553,160 A * 9/1996 Dawson ........................ 382/166
7,747,068 B1 * 6/2010 Smyth et al. .................. 382/154

* cited by examiner

*Primary Examiner* — Theresa T Doan
(74) *Attorney, Agent, or Firm* — Law Offices of Robert F. Zielinski, LLC

(57) ABSTRACT

A device has means for computing and obtaining blood vessel extraction images by extracting blood vessel portions from two or more fundus images, means for computing and obtaining a corner data image having corner portions of the blood vessel portions detected from the obtained blood vessel extraction image, means for computing and obtaining a probability distribution diagram for the corner data image by convolving the corner data image with a window function, means for computing a matching probability score when executing a matching processing between two or more fundus images on the basis of the probability distribution diagram corresponding to each fundus image obtained and the corner data image, and means for creating a retinal fundus map by superimposing two or more fundus images on the basis of the obtained matching probability score.

11 Claims, 14 Drawing Sheets

DEVICE AND METHOD FOR CREATING RETINAL FUNDUS MAPS

CROSS-REFERENCE TO RELATED PATENT APPLICATIONS

This application claims priority under 35 U.S.C. §119(a) to Japanese Patent Application No. 2007-290685, filed Nov. 8, 2007, the entirety of which is hereby incorporated by reference.

BACKGROUND OF THE INVENTION

The invention relates to a device and a method for creating retinal fundus maps by combining two or more retinal fundus images.

In a previously known device for combining two or more retinal fundus images to create a retinal fundus map (retinal image montage), intersections between blood vessels which are shown in each fundus image are extracted as characteristic points, and correlation matching is executed on image data which are at a periphery of the intersections of blood vessels in two sheets of fundus images to find a pair having a common intersection, and two fundus images are superimposed on each other with the found intersection pair as a standard so as to create a retinal fundus map. Such technique is disclosed in Japanese patent application publication No. 2000-23921.

If photographic conditions (which may be changed according to a value of gamma, existence of optic disk, state of flare, or quantity of blood vessels) are not constant at the time of matching for blood vessel intersections, correct correspondence between the intersections is not ensured, and this matching lacks credibility. Since the matching of intersections is executed on image data, pixel data are matched with each other. Then, computational load is rather high, and it takes longer time for processing thereby. And, two or more fundus images to be compounded respectively need to have intersections of blood vessel to be matched. Therefore, it is necessary to obtain fundus images in advance so as to include such a common intersection of blood vessel when obtaining fundus images. That is, a skill for obtaining such fundus images is necessary for testers.

The invention has been made under the above-mentioned circumstances, and the object of the invention is to provide a device and method for creating retinal fundus maps wherein a stable matching is possible even if photographic conditions (which may be changed according to a value of gamma, existence of optic disk, state of flare, or quantity of blood vessels) are not constant, the computational load at the time of the matching can be reduced, and no skill is necessary for testers when obtaining fundus images.

SUMMARY OF THE INVENTION

One aspect of the invention is device for creating retinal fundus maps in such a manner that two or more fundus images are obtained for the same eye to be examined by changing a relative position of objective lens of a fundus camera with respect to said eye to be examined and thus obtained fundus images are arranged, being superimposed on each other, comprising:

a memory for storing two or more sheets of fundus images for the same eye to be examined which are obtained by said fundus camera;

blood vessel extraction image obtaining means for computing and obtaining blood vessel extraction images by extracting blood vessel portions from said obtained two or more fundus images;

corner data image obtaining means for computing and obtaining a corner data image having corner portions of said blood vessel portions detected from said obtained blood vessel extraction image;

probability distribution diagram obtaining means for computing and obtaining a probability distribution diagram for said corner data image by convolving said corner data image with a window function;

matching score computing means for computing a matching probability score when executing a matching processing between said two or more fundus images on the basis of said probability distribution diagram corresponding to said each fundus image obtained and said corner data image, and for storing its result in a memory; and image compounding means for creating a retinal fundus map by superimposing said two or more retinal fundus images on the basis of said obtained matching probability score.

According to this aspect of the invention, the matching processing can be executed if blood vessel portions are only photographed regardless of presence of specific portions, such as branch portions of blood vessels since the matching processing is executed by detecting the corner portions of the blood vessel extraction image having blood vessel portions extracted from the fundus image, and stable matching is possible even if photographic conditions (which may be changed according to a value of gamma, existence of optic disk, state of flare, or quantity of blood vessels) are not constant.

Besides, at the time of the matching processing, the probability distribution diagram is computed and obtained for the corner data image which shows the characteristic point data which are corner portions detected from blood vessel portions from the corner data image by convolving with a window function, and the matching processing between two or more fundus images is executed on the basis of the probability distribution diagram and corner data image by computing the matching probability score, so that computational volume for computing the matching probability score can be widely decreased in comparison with the correlation matching processing between pixels of original fundus images, and the processing in a short time is possible And, this matching processing is not executed between the pixels of both fundus images FI, but is executed between the probability distribution diagram (Pn) and the corner data image (CD, $T_{n+1}$), so that this matching processing has a robustness since a statistical detection is possible even if a correspondence between the detected characters is not always taken between both images, such as photographic conditions of the original fundus images FI (which may be changed according to a value of gamma, existence of optic disk, state of flare, or quantity of blood vessels) are not ideal (constant).

Another aspect of the invention is the device for creating retinal fundus maps, wherein said blood vessel extraction image obtaining means has 1) low spatial frequency component image producing means for obtaining a low spatial frequency component image by extracting an image having low spatial frequency components from said fundus image, and 2) low spatial frequency component removing means for computing and obtaining a low spatial frequency component removing image as said blood vessel extraction image by computing a difference between said obtained low spatial frequency component images from said fundus mage.

According to this aspect of the invention, low spatial frequency components, such as masks (black portions at a periphery of fundus image), unevenness of luminance, flare, optic disk and choroids, are removed by computing a difference of a low spatial frequency component image from the fundus image and computing and obtaining the low spatial frequency component removing image as the blood vessel extraction image, so that the image where blood vessel portions are left, that is, the image having extracted blood vessel portions (BP) can be obtained and subsequent procedure for detecting corner portions can be correctly executed for the blood vessel portions (BP), and the correct matching processing is possible.

Another aspect of the invention is the device for creating retinal fundus maps, wherein said low spatial frequency component image producing means has morphology processing means for obtaining said low spatial frequency component image by executing a morphology processing on said fundus image.

According to this aspect of the invention, the low spatial frequency component image can be easily obtained by the morphology processing.

Another aspect of the invention is the device for creating retinal fundus maps, wherein said corner data image obtaining means has 1) corner image obtaining means for obtaining a corner detection image having corners of said blood vessel portions detected on said obtained blood vessel extraction image from said blood vessel extraction image which has been obtained, and 2) corner data image obtaining means for computing and obtaining an image after removing pixel data of said fundus image which are left on said corner detection image from said corner detection image as a corner data image.

According to this aspect of the invention, the image from which pixels of the original fundus image are removed, which is suitable for subsequent matching processing, can be produced by the corner image obtaining means and the corner data image obtaining means.

Another aspect of the invention is the device for creating retinal fundus maps, wherein said corner image obtaining means has Harris operator processing means for detecting corners from said blood vessel portions with Harris operator.

According to this aspect of the invention, preferably, Harris operator which is a well known corner detecting method can be used.

Another aspect of the invention is the device for creating retinal fundus maps, wherein said matching score computing means has 1) matching processing means for executing matching processing on both images by superimposing corner data images which correspond to the fundus images excluding some fundus image on a probability distribution diagram of some fundus image one by one and changing relative displacement volume of both images, and 2) score computing means for computing said matching probability score of predetermined bounds by changing said relative displacement volume within said predetermined bounds.

According to this aspect of the invention, the other fundus image which matches one fundus image can be effectively found.

Another aspect of the invention is the device for creating retinal fundus maps, wherein said matching processing by said matching processing means is executed on only an area overlapping between said probability distribution diagram and said corner data image.

According to this aspect of the invention, the matching processing is executed by the extremely simple computation for only overlapping area, so that the computational volume necessary for the matching processing can be widely reduced.

Another aspect of the invention is the device for creating retinal fundus maps, wherein said image compounding means has 1) threshold value judging means for comparing said matching probability scores between respective said fundus images which have been computed by said matching score computing means so as to judge whether or not in connection with some fundus image, there is said fundus image rather than said some fundus image which score exceeds a predetermined threshold value, and 2) image selection means for selecting the other said fundus image wherein said score exceeding a predetermined threshold value has been computed in connection with some fundus image if there is and determining it as a fundus image which is to be connected with said some fundus image, and 3) image arrangement means for superimposing said the other fundus image selected and said some fundus image on each other so as to create a retinal fundus map.

According to this aspect of the invention, the fundus image to be connected with some fundus image is selected and determined on the basis of a predetermined threshold value, so that a retinal fundus map can be effectively formed.

Another aspect of the invention is the device for creating retinal fundus maps, further comprising color judgment means for judging two or more fundus images for the same eye to be examined which have been obtained by said fundus camera to be color images or gray images, and luminance inversion means for inverting luminance gradation of said fundus image if said color judgment means judges said fundus image to be a gray image, said device wherein said blood vessel extraction image obtaining means computes and obtains a blood vessel extraction image having extracted blood vessel portions with said fundus image which luminance gradation has been inverted by said luminance inversion means if said fundus image has been judged to be a gray image.

According to this aspect of the invention, even if the fundus image is a gray image, its brightness gradation is inverted, so that blood vessels can be smoothly extracted in a subsequent processing.

Another aspect of the invention is the device for creating retinal fundus maps, wherein said color judgment means has 1) difference image producing means for producing a difference image of each color element which comprises said fundus image, and 2) gray image judgment means for computing a standard deviation of said difference image and judging to be a gray image if said value is a color judgment threshold value or less.

According to this aspect of the invention, a gray image can be easily judged even if color/gray data are not stored at the time of obtaining fundus images.

Another aspect of the invention is a method of creating retinal fundus maps in such a manner that two or more fundus images are obtained for the same eye to be examined by changing a relative position of objective lens of a fundus camera with respect to said eye to be examined and thus obtained fundus images are arranged, being superimposed on each other, comprising:

a step of obtaining two or more fundus images of said the same eye to be examined by said fundus camera;

a step of computing and obtaining a blood vessel extraction image having blood vessel portions which are extracted from said two or more fundus images;

a step of computing and obtaining a corner data image having corner portions of said blood vessel portions which are detected from said obtained blood vessel extraction image;

a step of computing and obtaining a probability distribution diagram for said corner data image by convolving said corner data image with a window function;

a step of executing a matching processing between said two or more fundus images on the basis of said probability distribution diagram corresponding each said obtained fundus image and said corner data image so as to compute a matching probability score at the time of said matching processing, and storing the result in a memory; and a step of arranging said two or more fundus images, being superimposed on each other on the basis of said obtained matching probability score so as to create a retinal fundus map.

BEST MODE FOR EXECUTING THE INVENTION

An embodiment of the invention will now be explained, referring to appended figures.

Figure 1:
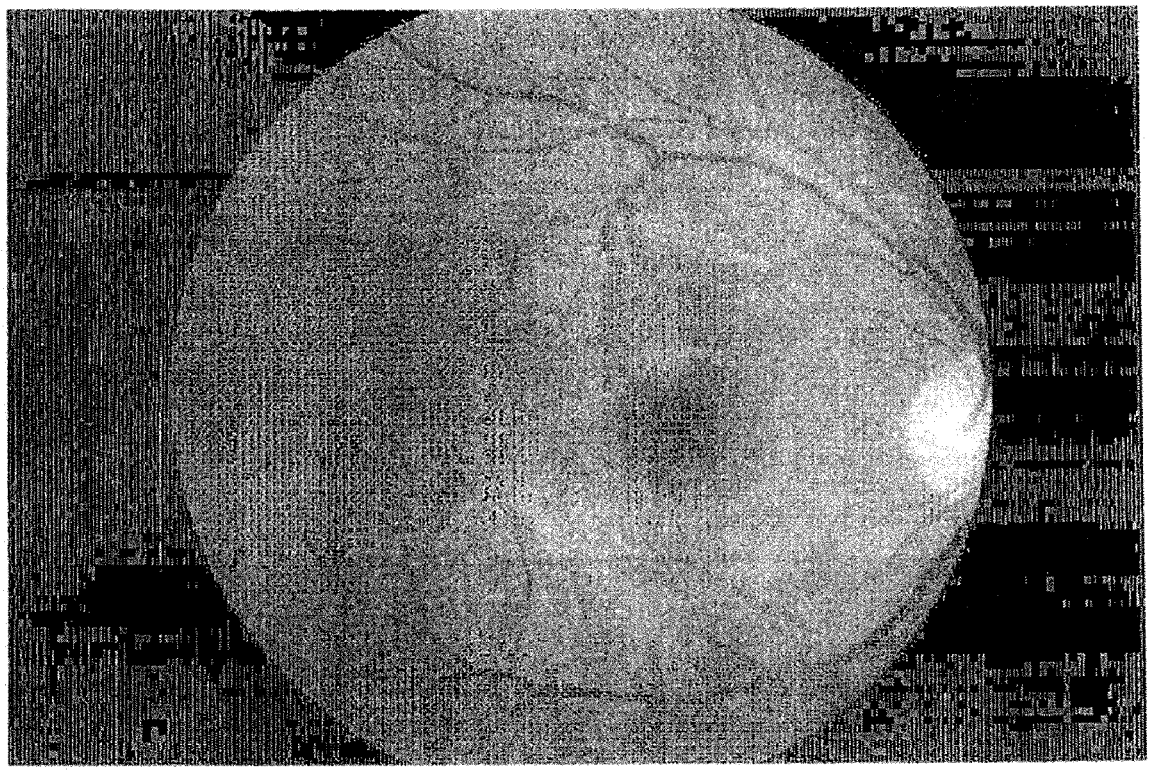
FIG. 1 is one of a series of fundus images of the same eye to be examined, which are obtained by a fundus camera.
Figure 2:
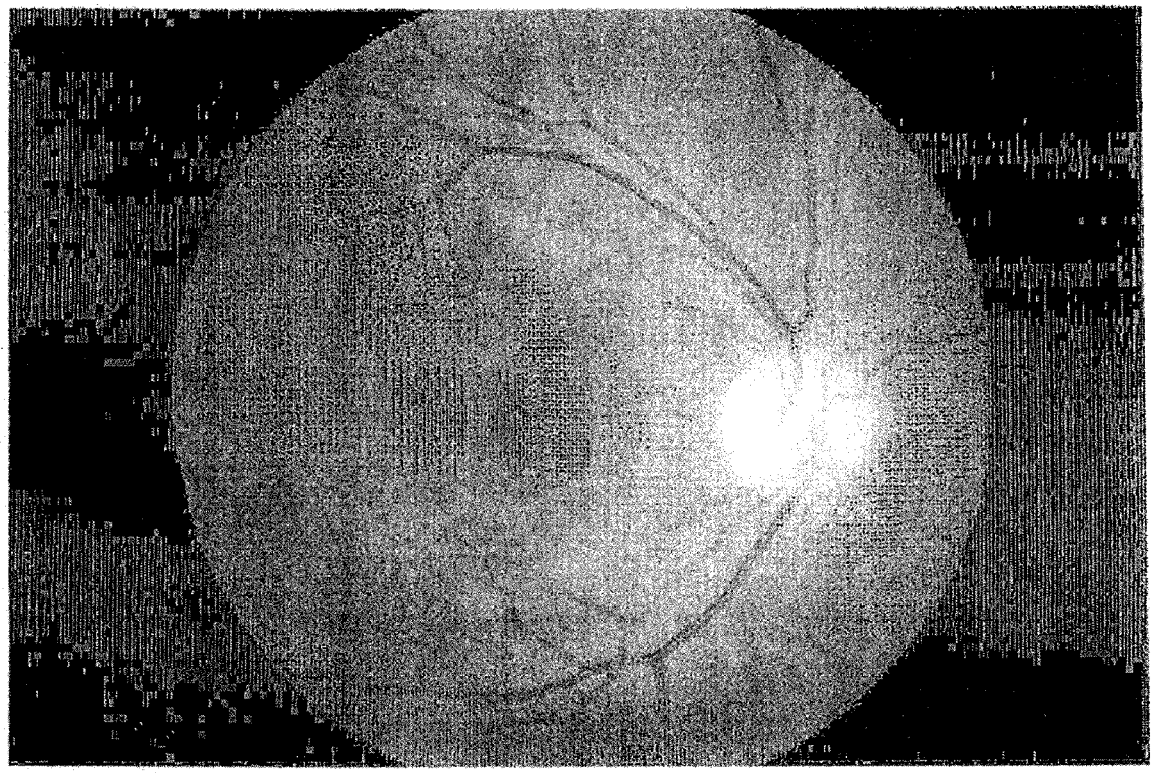
FIG. 2 is one of a series of fundus images of the same eye to be examined, which are obtained by the fundus camera.
Figure 3:
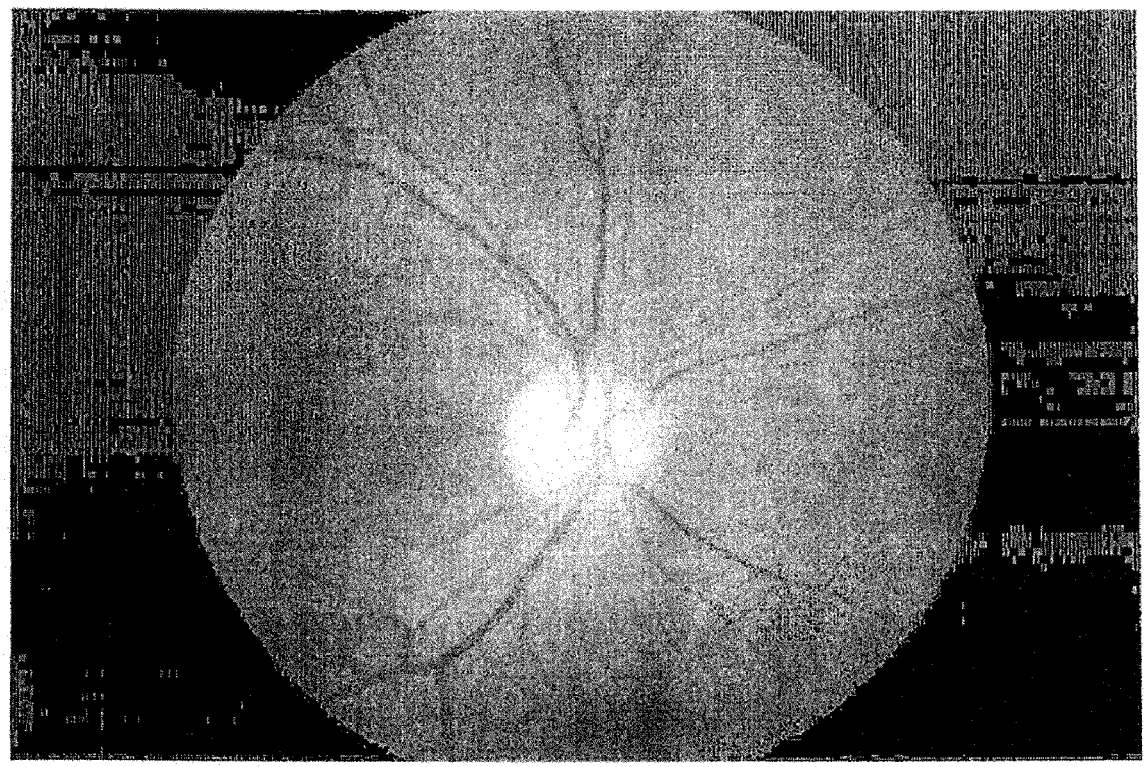
FIG. 3 is one of a series of fundus images of the same eye to be examined, which are obtained by the fundus camera.
Figure 4:
FIG. 4 is an enlarged view of the fundus image.
Figure 5:
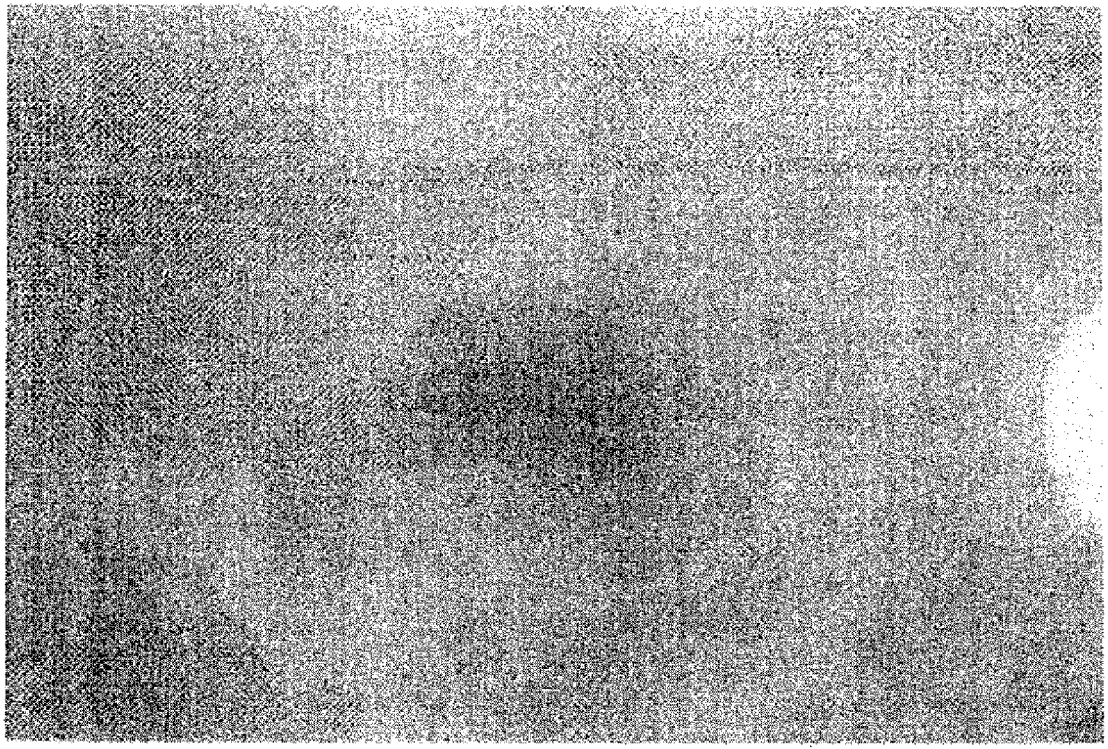
FIG. 5 is a view of the image after spatial frequency components lower than blood vessel components are extracted from the image of FIG. 4.
Figure 6:
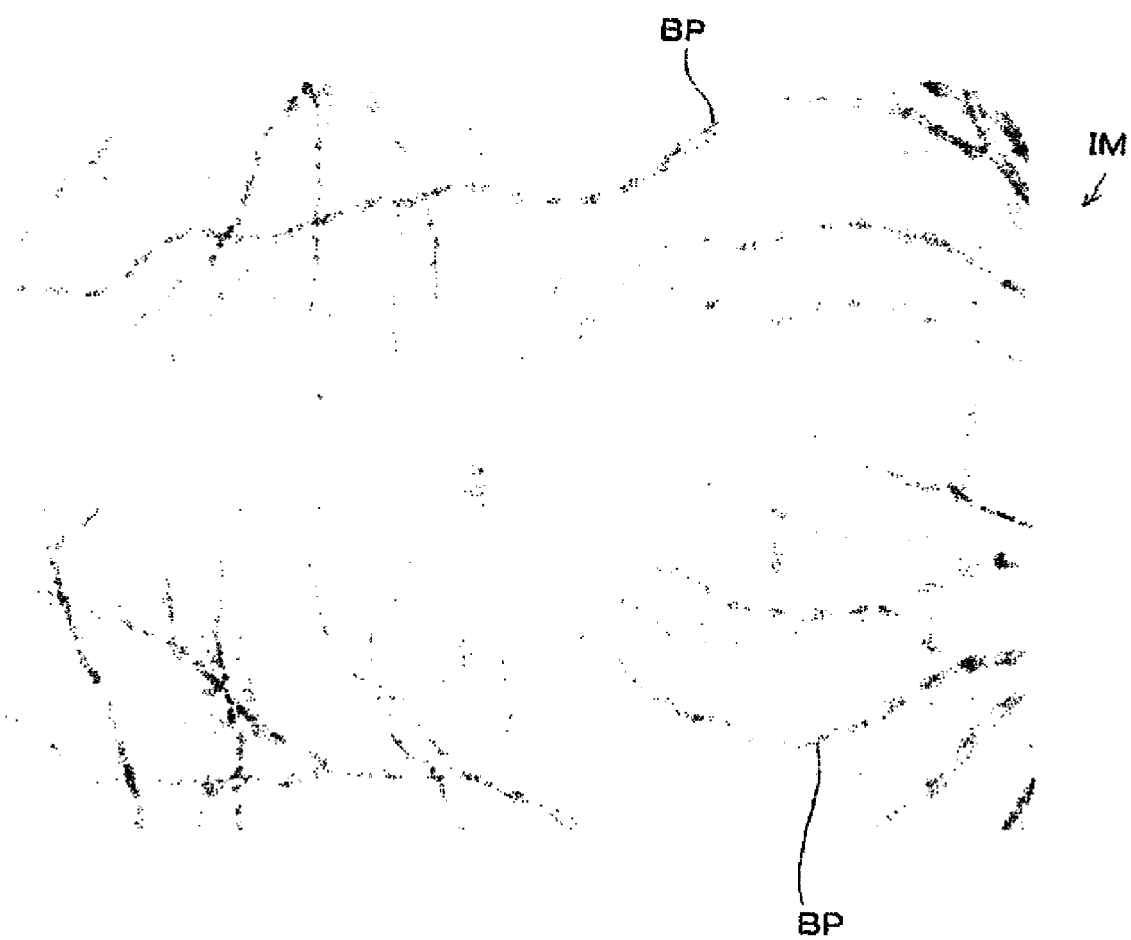
FIG. 6 is a view of the image after the low spatial frequency components in FIG. 5 are removed from the image of FIG. 4.
Figure 7:
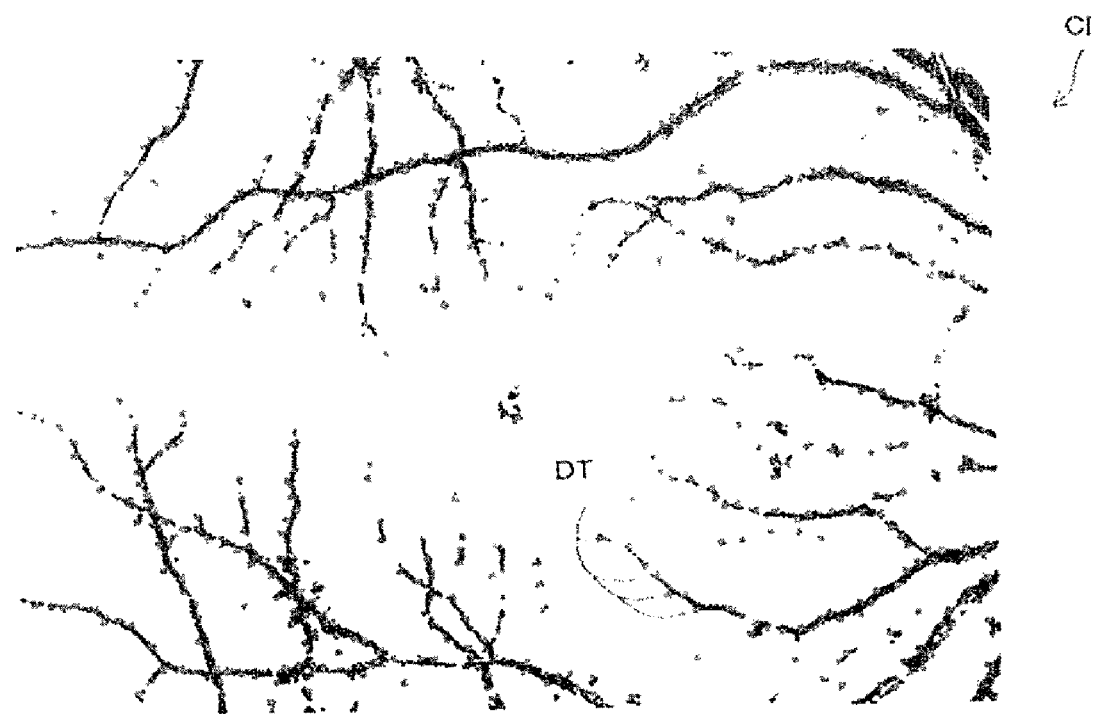
FIG. 7 is a view of the image after detecting corner characteristic points of blood vessels from the image of FIG. 6.
Figure 8:
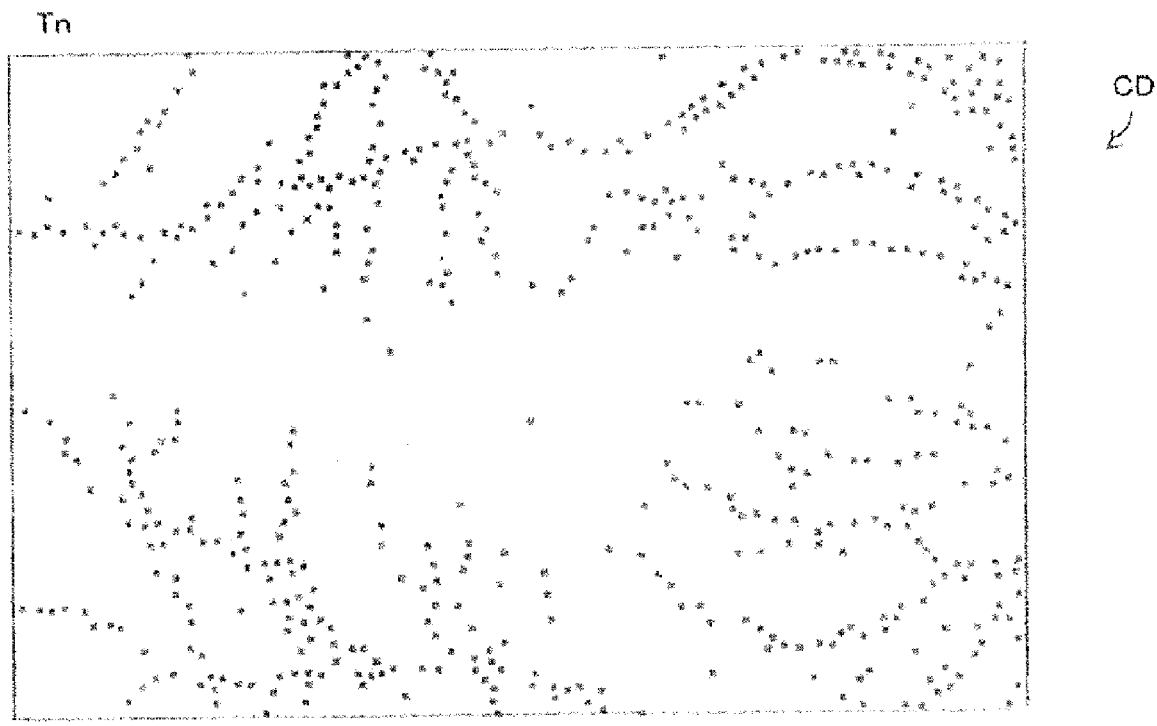
FIG. 8 is an image of only the corner characteristic points after removing the original blood vessels image from the image of FIG. 7.
Figure 9:
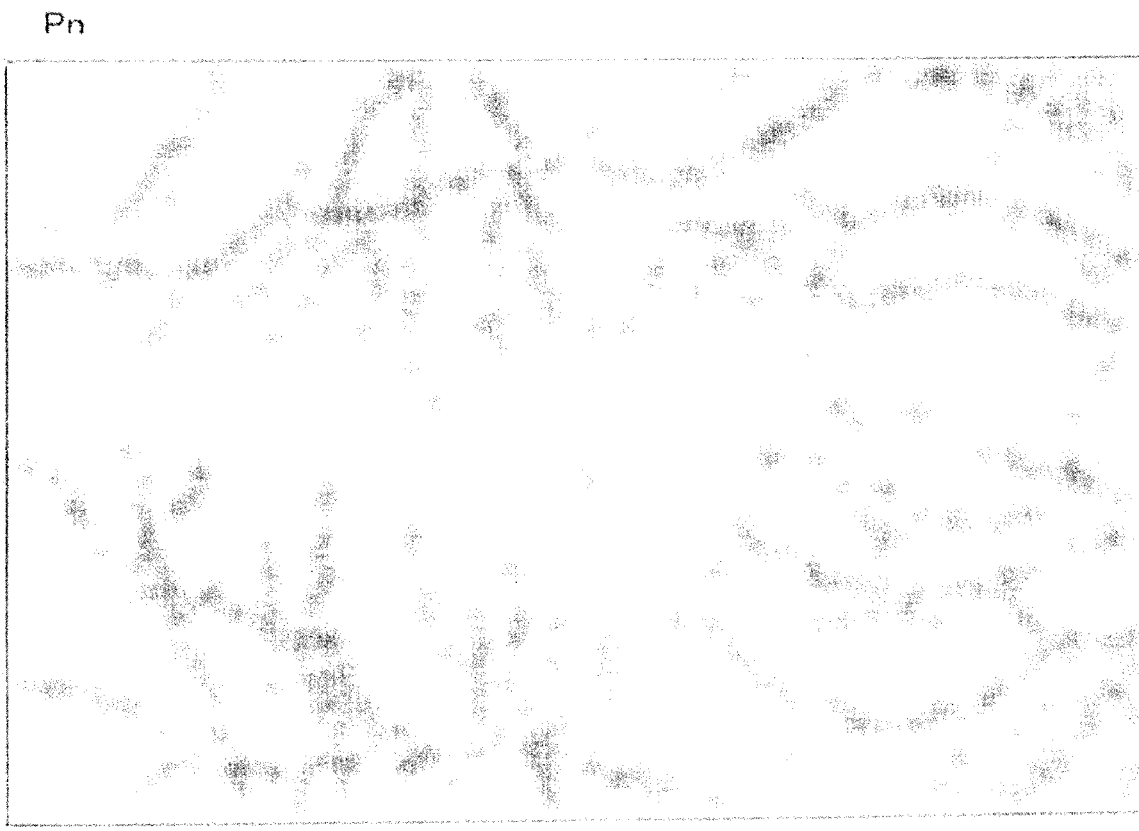
FIG. 9 is an image which is converted from the image of the corner characteristic points of FIG. 8 into a probability distribution diagram.
Figure 10:
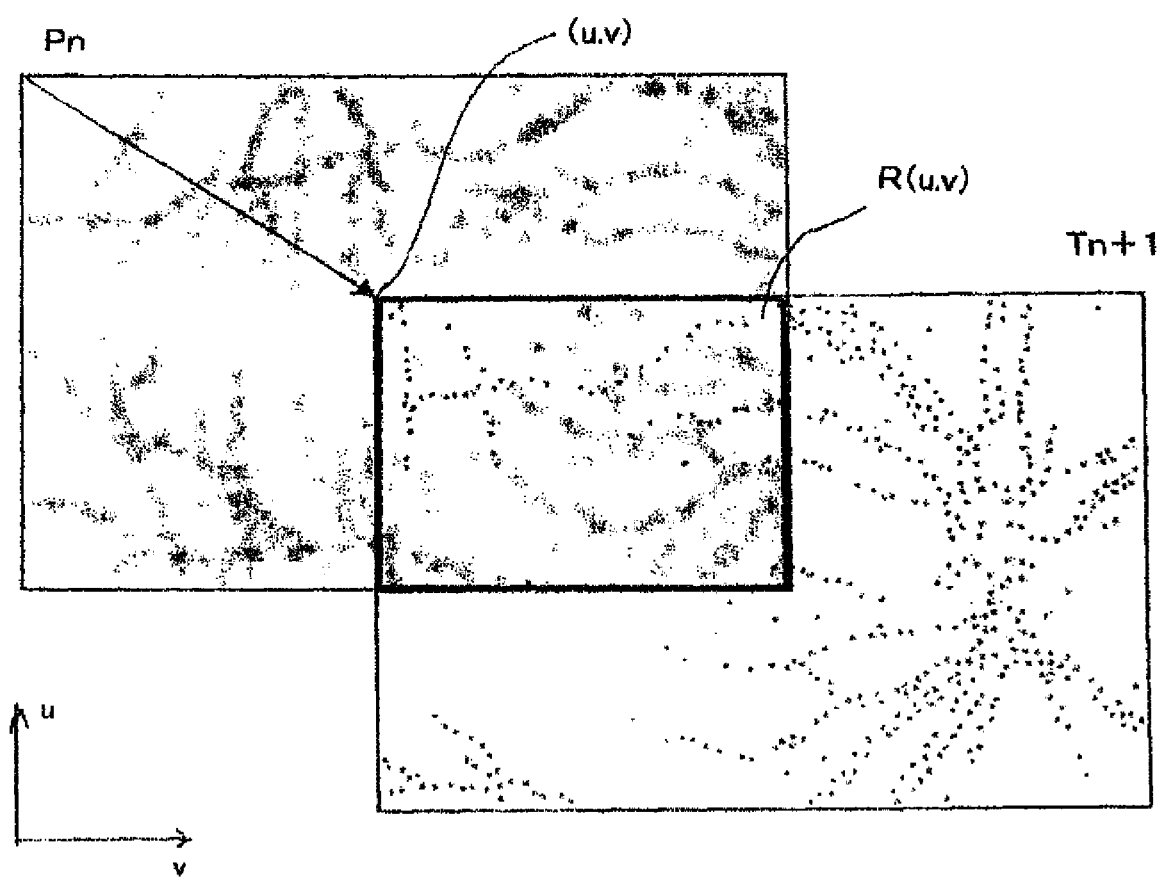
FIG. 10 is a view showing a routine of computing a probability score of matching by superimposing the image of the probability distribution diagram and the image of the corner characteristic points.
Figure 11:
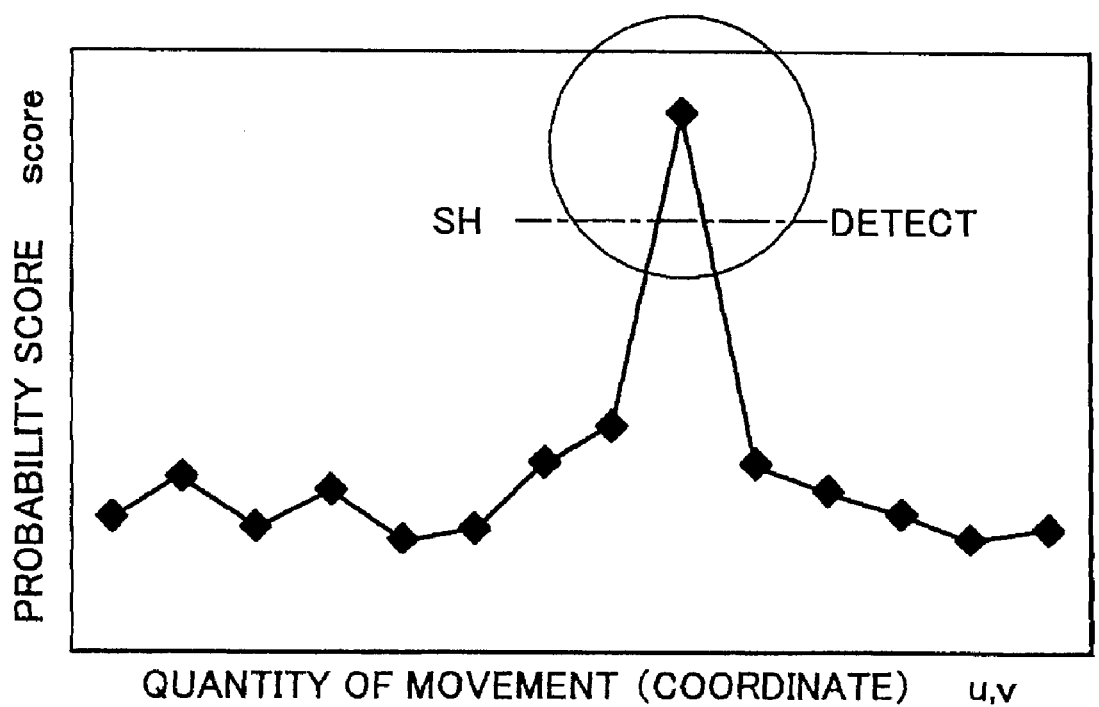
FIG. 11 is a view showing a relationship between obtained amount of movement and the score of the probability distribution diagram.
Figure 12:
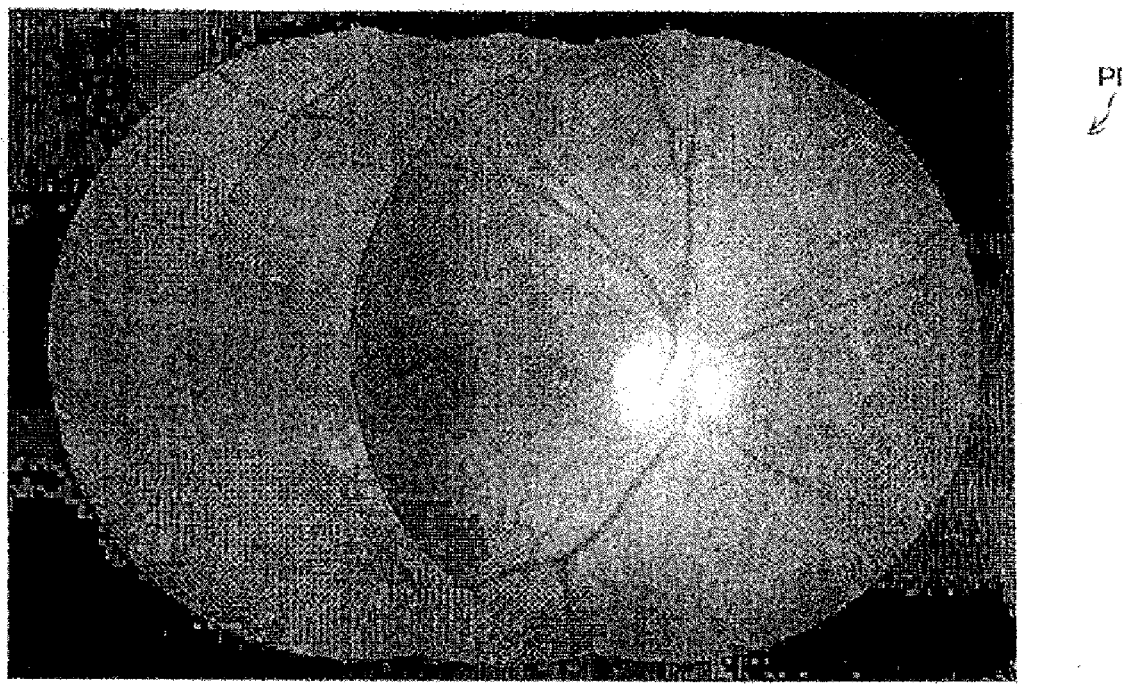
FIG. 12 is a view of the retinal fundus map created.
Figure 13:
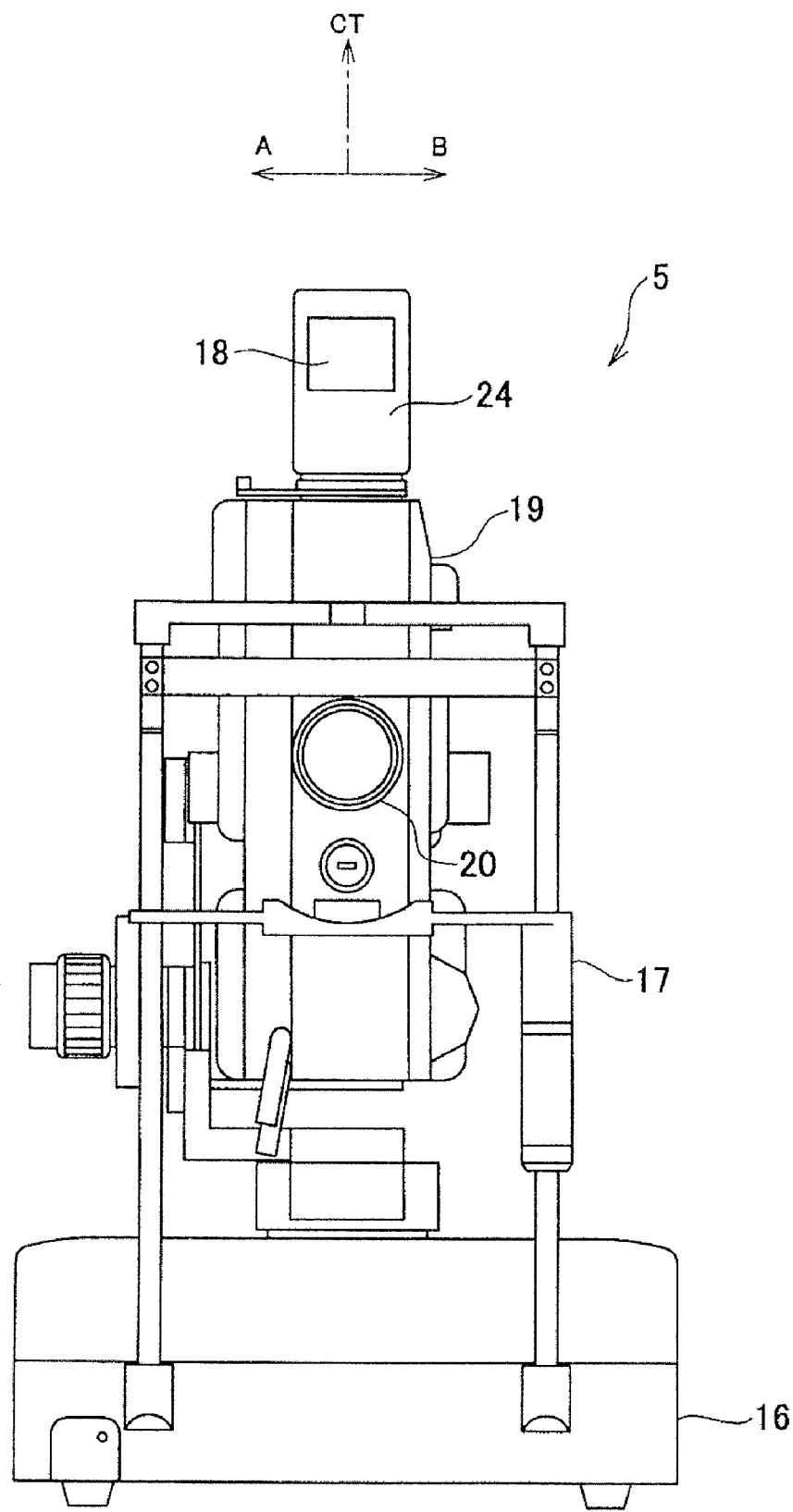
FIG. 13 is a front view showing the fundus camera.
Figure 14:
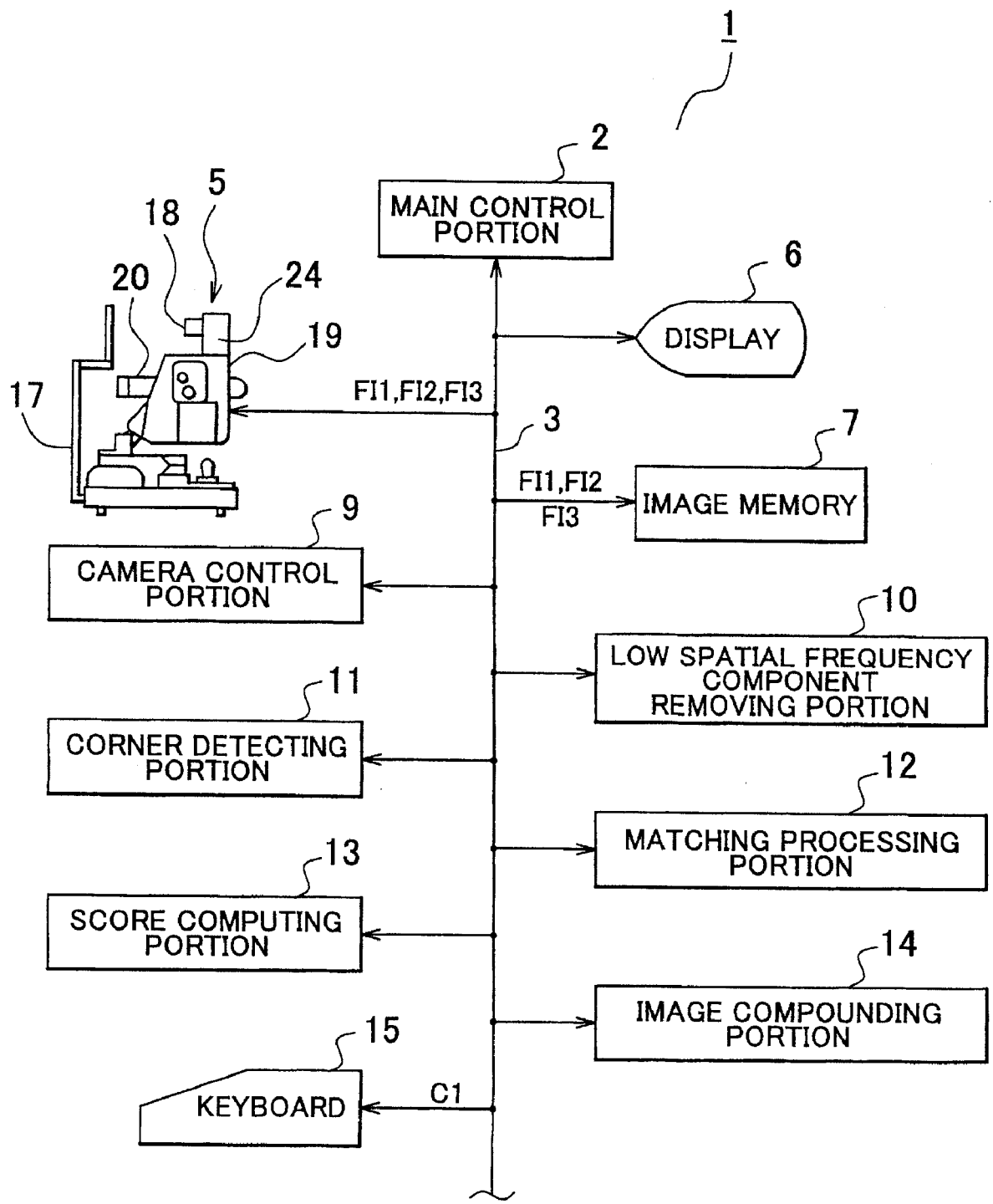
FIG. 14 is a block diagram showing a device for creating retinal fundus maps, to which the present invention is applied.

FIGS. 1 to 3 are views of a series of fundus images of the same eye to be examined, which are obtained by a fundus camera, FIG. 4 is an enlarged view of the fundus image, FIG. 5 is a view of the image after spatial frequency components lower than blood vessel components are extracted from the image of FIG. 4, FIG. 6 is a view of the image after the low spatial frequency components in FIG. 5 are removed from the image of FIG. 4, FIG. 7 is a view of the image after detecting corner characteristic points of blood vessels from the image of FIG. 6, FIG. 8 is an image of only the corner characteristic points after removing the original blood vessels image from the image of FIG. 7, FIG. 9 is an image which is converted from the image of the corner characteristic points of FIG. 8 into a probability distribution diagram, FIG. 10 is a view showing a routine of computing a probability score of matching by superimposing the image of the probability distribution diagram and the image of the corner characteristic points, FIG. 11 is a view showing a relationship between obtained amount of movement and the score of the probability distribution diagram, FIG. 12 is a view of the retinal fundus map created, FIG. 13 is a front view showing the fundus camera, and FIG. 14 is a block diagram showing a device for creating retinal fundus maps, to which the present invention is applied.

As shown in FIG. 14, a device 1 for creating retinal fundus maps has a main control portion 2, and a fundus camera 5, a display 6, an image memory 7, a camera control portion 9, a low spatial frequency component removing portion 10, a corner detecting portion 11, a matching processing portion 12, a score computing portion 13, an image compounding portion 14 and a keyboard 15 are connected with the main control portion 2 via a bus line 3.

As shown in FIG. 13, the fundus camera 5 has a base 16, and the base 16 is provided with a jaw stand so as to support a face of an examinee with respect to a camera body. The camera body 19 is provided on the base 16 so as to be freely moved within predetermined bounds in a horizontal direction, that is, a direction as shown by arrows A and B in the figure, and the camera body 19 has objective lens 20, facing an eye to be examined of an examinee which is to be photographed. Besides, a CCD camera 18 is connected with an upper portion of the camera body 19 in the figure through a relay lens unit 24.

In order to create a retinal fundus map of a retinal fundus of an examinee with the device 1 for creating retinal fundus maps by combining two or more fundus images which has the above-mentioned structure, firstly, a jaw of an examinee is put on the jaw stand 17 so as to face the eye to be examined to the camera body 19. Subsequently, an examiner moves the camera body 19 in A direction or in B direction of FIG. 13 so that a right eye or a left eye of the examinee can be faced to the objective lens 20.

The examiner obtains the fundus image of the examinee by operating an appropriate operation button (not shown) on the keyboard 15 in the above-mentioned state so as to drive the funds camera 5 through the camera control portion 9. On this occasion, two or more fundus images are obtained for the same eye to be examined by changing a position of the objective lens 20 relative to the eye to be examined in order to photograph a wider scope of the fundus of the eye to be examined. As shown in FIGS. 1 through 3, thus obtained images are fundus images FI1, FI2, FI3. Since the obtained fundus images FI1, FI2, FI3 are ones of the same eye to be examined, there are some fundus images of the two or more fundus images which have a common scope of the fundus. This does not means that all fundus images of the same eye to be examined have always the common scope of the fundus, but means that there is a common scope of the fundus between two or more fundus images obtained and the common fundus areas are not always the same.

Finally, one big panoramic fundus image is formed by connecting two or more fundus images FI1, FI2 and FI3 obtained with each other, superimposing the common scopes of the fundus of the respective fundus images on each other.

The details of the abovementioned routines is now explained. The main control portion 2 stores two or more fundus images FI1, FI2 and FI1 which have been obtained for the same eye to be examined with the fundus camera 5 by changing the relative position between the lens and the eye to be examined in the image memory 7. Subsequently, an examiner instructs to compound the fundus images of the eye to be examined so as to create a retinal fundus map through an operation of the keyboard 15. If a retinal fundus map creating instruction C1 is outputted, the main control portion 2 instructs the low spatial frequency component removing portion 10 to judge whether two or more fundus images obtained FI1, FI2 and FI3 are color images or gray images ("images in the case of fluorescence photography" hereinafter).

Generally, there are two types fundus images, color images and gray images. In the case of color images, blood vessel portions are darker than peripheral portions (low luminance), and in case of gray (fluorescence) images, blood vessel portions are brighter than peripheral portions (high luminance). At the time of the procedure for removing low spatial frequency components which will be described hereinafter, whether the obtained fundus images FI1, FI2 and FI3 are color images or gray image is judged so as not inadvertently remove blood vessel portions, and corresponding procedures are executed.

A method of judging whether the obtained fundus images FI1, FI2 and FI3 are color images or gray (fluorescent) images is that data which show color image or gray (fluorescent) image as attribute data of each image are stored as color information at the time of photographing fundus images, and such judgment is executed by reviewing the color information, or from pixel information of the respective fundus images FI1, FI2 and FI3 by the following image processing.

That is, whether the fundus image is a color image or a gray (fluorescent) image is judged from the pixel information of the respective fundus images FI1, FI2 and FI3. In order to do so, difference images of respective color elements, such as R (red), G (green) and B (blue) which comprise an image of the fundus image are produced, and standard deviations of the difference images are obtained so as to be judged. But, the judging method is not limited to such a method.

The low spatial frequency component removing portion 10 forms a color difference image with the following Formula for the n-th image.

$$C_n(i, j) = \left| \frac{R_n(i, j) + B_n(i, j)}{2} - G_n(i, j) \right| \quad \text{[Formula 1]}$$

where n denotes image number, Rn, Bn, Gn are respectively color planes of the n-th image A standard deviation σn of the thus obtained difference image Cn is computed. If this value is a threshold value for judging color or smaller, a color profile of the n-th image is judged to be a gray image. That is, $$Gray_n = \begin{cases} \text{True}, & \sigma_n < \text{Threshold} \\ \text{False}, & \text{Otherwise} \end{cases} \quad \text{[Formula 2]}$$

where Threshold is a normal threshold value for judgment.

The above-mentioned processing is executed on N sheets of input images, and the obtained fundus image is judged to be a color image or a gray image when the color profiles of all images are ones for a color image or a gray image. In case of a gray image, blood vessel portions are brighter (high luminance) than the periphery thereof. Then, luminance gradation of all images is inverted so as to darken (low luminance) the blood vessel portions rather than the periphery thereof in order to smoothly execute blood vessel extracting procedure which is described hereinafter. In the case of a color image, blood vessel portions are darker than the periphery thereof (low luminance) as described before. Then, no procedure is executed at this stage since it is possible to execute the blood vessel extracting procedure in the present condition.

At the time of preparing color difference image, a color model is converted from RGB into HSV, and similar processing can be also executed on saturation layer.

The procedure for judging to be a color image or a gray (fluorescence) image is thus executed on the obtained fundus images FI1, FI2 and FI3. If the obtained fundus images FI1, FI2 and FI3 are gray (fluorescence) images, a procedure for inverting luminance gradation is executed on the obtained fundus images FI1, FI2 and FI3, and the low spatial frequency component removing portion 10 enters the next procedure.

That is, the low spatial frequency component removing portion 10 executes a processing of removing low spatial frequency components, such as optical disk and flare, from the fundus images FI1, FI2 and FI3 on the basis of the instruction from the main control portion 2.

The low spatial frequency component removing portion 10 computes and obtains an image after removing high spatial frequency components, such as blood vessel components which luminance is relatively low, from each of the fundus images FI1, FI2 and FI3, that is, the image after passing through flare, optic disk and choroids in the fundus image FI as a low spatial frequency component image LG. For instance, as shown in FIG. 5, the low spatial frequency component image LG is extracted from the fundus image FI1 (partially shown) as shown in FIG. 4.

This processing is actualized by acting on the fundus image FI1 with morphology, for instance, as a low pass filter. The similar processing is executed on the other fundus images FI2 and FI3 although the specification refers to only fundus image FI1. Besides, common processing among the fundus images FI1, FI2 and FI3 is explained as the fundus image FI without differentiating the fundus images FI1, FI2 and FI3 from each other. In such a case, an object of this processing is to pass through the spatial frequency components, such as flare, optic disk and choroid, which are lower than blood vessel components, so that a structure which is bigger than the maximum value of a thickness of blood vessel in the image is selected as a structural element. In FIG. 4 for instance, a structural element of true circle of radius 20 pixels is used for 1.4 megapixel fundus image. A smoothing filter, Fourier transform, wavelet can be applied as a low pass filter as well as morphology.

The low spatial frequency component removing portion 10 computes and extracts the difference between the fundus image FI in FIG. 4 and the low spatial frequency component image LG which has been extracted from the fundus image FT on the basis of both images, and computes and obtains the low spatial frequency component removing image as shown in FIG. 6 as a blood vessel extraction image IM. The low spatial frequency component removing image IM is an image having extracted blood vessel portions BP wherein the low spatial frequency components, such as flare, optic disk and choroids, are removed from the fundus image FI, and at the result, high spatial frequency components, such as blood vessels, are left. Furthermore, the low spatial frequency component removing portion 10 executes such a processing that the other noise image portions (noise in the shape of a thin spot in FIG. 6), which have not been removed from the blood vessel extracting image IM of FIG. 6 by the low spatial frequency component removing processing are removed with a well-known noise removal processing computing, such as the before-mentioned morphology processing so as to clearly extract the blood vessel portions BP of the blood vessel extracting image IM. At the same time, adjustment is executed so as to make a contrast of the blood vessel components BP of all images in order to extract the blood vessel components BP more clearly. Such a processing can be easily executed since the low spatial frequency components have already been removed, as described before.

After thus producing the blood vessel extracted images IM by extracting blood vessel portions BP from all fundus images FI through the low spatial frequency component removing portion 10, the main control portion 2 instructs the corner detecting portion 11 to execute a corner detection procedure of extracting points which curvature is large (sharply curved points) from the blood vessel extracting image IM on the basis of this image IM.

Receiving this instruction, the corner detecting portion 11 executes a procedure of obtaining a corner detection image CI by extracting corner portions of the blood vessel portions BP from the blood portions BP shown on the blood vessel extracting image IM with a well-known corner detection method, as shown in FIG. 7. Such a processing can be executed by Harris operator, but the other corner detection methods, such as SUSAN operator, FAST feature extraction, Minimum eigenvalue method, can be also used. In a case of FIG. 7, detected corners are shown with points DT. At this point of time, the image shown in the blood vessel extracting image IM is almost comprised of the blood vessel portions BP, and the low spatial frequency components, such as flare, optic disk and choroids, have been removed, so that the corners which have been detected by the corner detection processing are estimated to be corners in connection with the blood vessel portion BP with a high probability.

After thus obtaining the corner detection image CI, the corner detecting portion 11 computes and obtains a corner data image CD which is comprised of only points DT which show corners, as shown in FIG. 8 by removing pixel data of the original fundus image FI which is comprised of the low spatial frequency component removing image IM from the corner detection image CI. The corner data image CD is the image obtained by extracting the corner portions of the blood vessel portions BP from the fundus image FI as points DT.

Subsequently, the corner detecting portion 11 executes a processing of convolving the obtained corner data image CD with an optical window function so as to convert the corner data image CD and computing and obtaining a probability distribution diagram for the corner data image CD. Such a procedure is executed as follow.

C corner portions detected from the n-th image Gn, that is, corner feature points Fn ($x_c$, $y_c$) are developed on a coordinate plane Tn.

$$T_n(i, j) = \begin{cases} 1, & \text{if } (i, j) \in F_n \\ 0, & \text{Otherwise} \end{cases} \quad \text{[Formula 3]}$$

That is, Tn is a plane of feature point wherein a value at the coordinate where the feature point is detected is one (1), and the value is zero (0) otherwise.

Subsequently, a probability distribution diagram Pn is obtained as shown in FIG. 9 by convolving the plane of feature point Tn with an optional window function w. This shows a probability of existing correct feature points at each coordinate.

$$P_n = w * T_n \quad \text{[Formula 4]}$$

That is, $$P_n(i,j) = \Sigma_{k=-q}^{q}\Sigma_{l=-p}^{p} w(k,l) T_n(i-k, j-l) \quad \text{[Formula 5]}$$

where w is an optional window function having a size of (2p+1)×(2q+1), such as two-dimensional Gaussian window which has been expanded from one-dimensional one.

After thus obtaining the probability distribution diagrams Pn from the corner data image CD for all fundus images FT, the main control portion 2 instructs the matching processing portion 12 to execute a matching processing on the basis of the probability distribution diagrams Pn corresponding to the respectively obtained fundus images FI and the corner data image CD as shown in FIG. 10 in such a manner that the corner data images CD ($T_{n+1}$) corresponding to the fundus image $FI_{n+1}$ excluding some fundus image FIn are superimposed on the probability distribution diagram Pn corresponding to some fundus image FIn one by one, and the matching processing is executed between both images Pn and $T_{n+1}$ while relative displacement amount between both images, that is, coordinate shift amount (u, v) is changed. This matching processing is not executed between the pixels of both fundus images FI, but is executed between the probability distribution diagram Pn and the corner data image CD which is the feature point data. Therefore, this matching processing has a robustness since a statistical detection is possible even if a correspondence between the detected characters is not always taken between both images, such as even if photographic conditions of the original fundus images FI (which may be changed according to a value of gamma, existence of optic disk, state of flare, or quantity of blood vessels) are not ideal (constant). And, the matching processing is executed between the corner data image CD which is the feature point data and the probability distribution diagram Pn, as described above, so that computational complexity can be widely reduced in comparison with the matching processing between the pixel data of the fundus images FI. Then, the processing can be executed within a short time.

The matching processing is now explained in the concrete. If a coordinate shift between the n-th image Pn and the (n+1)th image $T_{n+1}$ is (u, v), the following operation is executed on only an overlapping area R(u,v) between the image Pn and the image $T_{n+1}$, as shown in FIG. 10.

$$f_{(u,v)} = \sum_{(i,j) \in R_{(u,v)}} T_{n+1}(i, j) \quad \text{[Formula 6]}$$

$$s_{(u,v)} = \sum_{(i,j) \in R_{(u,v)}} \begin{cases} P_n(i+u, j+v), & \text{if } T_{n+1}(i, j) = 2 \\ 0, & \text{if } T_{n+1}(i, j) = 0 \end{cases} \quad \text{[Formula 7]}$$

$$z_{(u,v)} = \sum_{(i,j) \in R_{(u,v)}} \begin{cases} 1, & \text{if } P_n(i+u, j+v) = 0 \land T_{n+1}(i, j) = 1 \\ 0, & \text{Otherwise} \end{cases} \quad \text{[Formula 8]}$$

Subsequently, the main control portion 2 instructs the score computing portion 13 to compute a matching probability score, Score (u, v) at the time when the shift between Pn and $T_{+1}$ is (u, v) with the above-mentioned result and to store the result in an appropriate memory. This probability score Score (u, v) is the probability of a correspondence between feature points of both images including deviation rate.

$$Score_{(u,v)} = \frac{s_{(u,v)}}{f_{(u,v)} - z_{(u,v)}} \times \frac{f^k_{(u,v)}}{z_{(u,v)}} \quad \text{[Formula 9]}$$

where k is a constant. Each Score (u, v) obtained with the following formula is computed in optional shift bounds (u,v). For instance, it is computed in the bounds of (−w<u<w, −h<v<h) by changing u and v. On this occasion, (w, h) is the image size of the image Pn and the image $T_{n+1}$ (both images have the same size of w×h).

After finishing the computation within the bounds, all scores stored in the memory are examined. If the score is a predetermined threshold value SH or higher as shown in FIG. 11, correct shift amount is considered to be detected, and the shift amount (u, v) at the time when the score is detected is determined as the shift amount between the fundus image FIn corresponding to the image Pn and the fundus image $FI_{n+1}$ corresponding to the image $T_{n+1}$. If two or more candidates exist, the highest score is selected. The thus detected shift amount (u, v) is the shift amount between the fundus image FIn and the fundus image $FI_{n+1}$ which corresponds to the image $T_{n+1}$.

After executing such a score computing procedure for all fundus images FI between the probability distribution diagram Pn of the fundus image FI and all corner data images CD corresponding to the other fundus images FI and storing the thus obtained score, Score (u, v) in a memory, the main control portion 2 instructs the image compounding portion 14 to connect two or more fundus images FI which have been obtained in connection with the same eye to be examined with each other so as to overlap with each other in order to create a retinal fundus map.

Receiving such an instruction, the image compounding portion 14 compares the scores of the respective fundus images FI which have been computed by the score computing portion 13 so as to judge whether or not the other fundus image FIm exists in which the score exceeding a predetermined threshold value SH in some fundus image FIn has been computed. If the other fundus image FIm exists, the other fundus image FIm where the score has been computed is determined as the fundus image FI to be connected with the fundus image FIn.

Such a fact that the score of the other fundus image FIm in connection with some fundus image FIn exceeds a predetermined threshold value SH means that the fundus images FIn and FIm correspond with each other at a high probability in their characteristic points (curves) in an overlapping area R (u,v) portion between both fundus images when superimposing the fundus images FIn and FIm on each other with some shift volume (u, v) in the matching processing as shown in FIG. 10. Then, the image compounding portion 14 judges that both fundus images FIn and FIm which exceed the threshold value SH are successive to each other, and superimposes both fundus images FIn, FIm on the basis of the shift volume (u, v) so as to take a positional relation as shown in FIG. 10.

In a similar way, a similar processing is executed on all fundus images FI so as to select the other fundus image FI to be connected with the fundus image FI with the threshold value SH as its standard, and both fundus images FI which have been selected are superimposed on the basis of the shift volume (u, v). By doing so, the obtained fundus images FI are compounded as a whole, being partially overlapped (overlapping area corresponds to R (u,v)), as shown in FIG. 12, and finally, a retinal fundus map PI is formed. The retinal fundus map PI which has been formed by the image compounding portion 14 is displayed on the display 6.

If two or more fundus images FIm exceed the threshold value SH in connection with one sheet of fundus image FIn and two or more candidates exist, the fundus image FIm having the highest score among these candidates is selected as the fundus image FIm to be connected with the fundus image FIn.

The above-mentioned embodiment is executed by using hardware means, such as the low spatial frequency component removing portion 10, the corner detecting portion 11, the matching processing portion 12, the score computing portion 13 and the image compounding portion 14. But, the all functions of the hardware or a part thereof can be time-dividedly executed by a computer with software in order to exercise similar effects. Such a device is included in the present invention.

The present invention is explained on the basis of the embodiment heretofore. The embodiment which is described in the present specification is illustrative and not limiting. The scope of the invention is designated by the accompanying claims and is not restricted by the descriptions of the specific embodiments. Accordingly, all the transformations and changes belonging to the claims are included in the scope of the present invention.

The invention claimed is:

1. Device for creating retinal fundus maps in such a manner that two or more fundus images are obtained for the same eye to be examined by changing a relative position of objective lens of a fundus camera with respect to said eye to be examined and thus obtained fundus images are arranged, being superimposed on each other, comprising:
   a memory for storing two or more sheets of fundus images for the same eye to be examined which are obtained by said fundus camera;
   blood vessel extraction image obtaining means for computing and obtaining blood vessel extraction images by extracting blood vessel portions from said obtained two or more fundus images;
   corner data image obtaining means for computing and obtaining a corner data image having corner portions of said blood vessel portions detected from said obtained blood vessel extraction image;
   probability distribution diagram obtaining means for computing and obtaining a probability distribution diagram for said corner data image by convolving said corner data image with a window function;
   matching score computing means for computing a matching probability score when executing a matching processing between said two or more fundus images on the basis of said probability distribution diagram corresponding to said each fundus image obtained and said corner data image, and for storing its result in a memory; and
   image compounding means for creating retinal fundus maps by superimposing said two or more fundus images on the basis of said obtained matching probability score.

2. The device for creating retinal fundus maps according to claim 1, wherein said blood vessel extraction image obtaining means has 1) low spatial frequency component image producing means for obtaining a low spatial frequency component image by extracting an image having low spatial frequency components from said fundus image, and 2) low spatial frequency component removing means for computing and obtaining a low spatial frequency component removing image as said blood vessel extraction image by computing a difference between said obtained low spatial frequency component images from said fundus image.

3. The device for creating retinal fundus maps according to claim 2, wherein said low spatial frequency component image producing means has morphology processing means for obtaining said low spatial frequency component image by executing a morphology processing on said fundus image.

4. The device for creating retinal fundus maps according to claim 1, wherein said corner data image obtaining means has 1) corner image obtaining means for obtaining a corner detection image having corners of said blood vessel portions detected on said obtained blood vessel extraction image from said blood vessel extraction image which has been obtained, and 2) corner data image obtaining means for computing and obtaining an image after removing pixel data of said fundus image which are left on said corner detection image from said corner detection image as a corner data image.

5. The device for creating retinal fundus maps according to claim 4, wherein said corner image obtaining means has Harris operator processing means for detecting corners from said blood vessel portions with Harris operator.

6. The device for creating retinal fundus maps according to claim 1, wherein said matching score computing means has 1) matching processing means for executing matching processing on both images by superimposing corner data images which correspond to the fundus images excluding some fundus image on a probability distribution diagram of some fundus image one by one and changing relative displacement volume of both images, and 2) score computing means for computing said matching probability score of predetermined bounds by changing said relative displacement volume within said predetermined bounds.

7. The device for creating retinal fundus maps according to claim 6, wherein said matching processing by said matching processing means is executed on only an area overlapping between said probability distribution diagram and said corner data image.

8. The device for creating retinal fundus maps according to claim 1, wherein said image compounding means has 1) threshold value judging means for comparing said matching probability scores between respective said fundus images which have been computed by said matching score computing means so as to judge whether or not in connection with some fundus image, there is said fundus image rather than said some fundus image which score exceeds a predetermined threshold value, and 2) image selection means for selecting the other said fundus image wherein said score exceeding a predetermined threshold value has been computed in connection with some fundus image if there is and determining it as a fundus image which is to be connected with said some fundus image, and 3) image arrangement means for superimposing said the other fundus image selected and said some fundus image on each other so as to create a retinal fundus map.

9. The device for creating retinal fundus maps according to claim 1, further comprising color judgment means for judging two or more fundus images for the same eye to be examined which have been obtained by said fundus camera to be color images or gray images, and luminance inversion means for inverting luminance gradation of said fundus image if said color judgment means judges said fundus image to be a gray image, said device wherein said blood vessel extraction image obtaining means computes and obtains a blood vessel extraction image having extracted blood vessel portions with said fundus image which luminance gradation has been inverted by said luminance inversion means if said fundus image has been judged to be a gray image.

10. The device for creating retinal fundus maps according to claim 9, wherein said color judgment means has 1) difference image producing means for producing a difference image of each color element which comprises said fundus image, and 2) gray image judgment means for computing a standard deviation of said difference image and judging to be a gray image if said value is a color judgment threshold value or less.

11. A method of creating retinal fundus maps in such a manner that two or more fundus images are obtained for the same eye to be examined by changing a relative position of objective lens of a fundus camera with respect to said eye to be examined and thus obtained fundus images are arranged, being superimposed on each other, comprising:

a step of obtaining two or more fundus images of said the same eye to be examined by said fundus camera;

a step of computing and obtaining a blood vessel extraction image having blood vessel portions which are extracted from said two or more fundus images;

a step of computing and obtaining a corner data image having corner portions of said blood vessel portions which are detected from said obtained blood vessel extraction image;

a step of computing and obtaining a probability distribution diagram for said corner data image by convolving said corner data image with a window function;

a step of executing a matching processing between said two or more fundus images on the basis of said probability distribution diagram corresponding each said obtained fundus image and said corner data image so as to compute a matching probability score at the time of said matching processing, and storing the result in a memory; and a step of arranging said two or more fundus images, being superimposed on each other on the basis of said obtained matching probability score so as to create a retinal fundus map.

* * * * *